United States Patent [19]
Conviser

[11] Patent Number: 6,132,679
[45] Date of Patent: Oct. 17, 2000

[54] METHOD AND APPARATUS FOR AERATING CHEMICALLY-STERILIZED ARTICLES

[75] Inventor: Stephen A. Conviser, Morristown, N.J.

[73] Assignee: AlliedSignal, Inc., Morristown, N.J.

[21] Appl. No.: 08/998,107

[22] Filed: Dec. 24, 1997

[51] Int. Cl.⁷ ...................................................... A61L 2/20

[52] U.S. Cl. ................................. 422/30; 422/33; 422/34

[58] Field of Search ................................. 422/1, 30, 31, 422/33, 34, 36

[56] References Cited

U.S. PATENT DOCUMENTS

| | | | |
|---|---|---|---|
| 4,770,851 | 9/1988 | Joslyn | 422/26 |
| 4,822,563 | 4/1989 | Joslyn | 422/34 X |
| 5,376,333 | 12/1994 | Shankland | 422/34 |
| 5,830,409 | 11/1998 | Childers et al. | 422/30 |

FOREIGN PATENT DOCUMENTS

WO 97/25075   7/1997   WIPO .

OTHER PUBLICATIONS

Good Hospital Practice: Ethylene oxide sterilization and sterility assurance ANSI/AAMI ST41–1992; pp. 235–272.
Kinetics of the aeration of ethylene–oxide sterilized plastics; by Vagn Handlos Biomaterials 1980, vol. 1 Jul., pp. 149–157.
Nancy J. Hermanson, *Effects of Alternate Carriers of Ethylene Oxide Steriliant on Thermoplastics*, Oct. 1 ,1 991.
James Whitbourne, Barry F.J. Page, and Duane T. Centola, *Ethylene Oxide Sterilization: Ethylene Oxide Residues*, Chapter 23, p. 200–208, prior art.
P. Vink and K. Pleijstier, *Aeration of ethylene oxide–sterilized polymers*, Biomaterials 1986, vol. 7, May 1986.
Joslyn Sterilizer Corporation, *Introducing a New Age in Serilization, The Joslyn 100% EtO Sterilizer*, prior art.

*Primary Examiner*—Elizabeth McKane
*Attorney, Agent, or Firm*—Jay P. Friedenson

[57] ABSTRACT

A method for aerating an ethylene oxide-sterilized article, said method comprising exposing said article to at least one co-adsorbate under conditions such that said co-adsorbate remains vaporized, said co-adsorbate having a partial pressure under said conditions sufficient to displace at least a portion of ethylene oxide adsorbed by said article.

15 Claims, 2 Drawing Sheets

METHOD AND APPARATUS FOR AERATING CHEMICALLY-STERILIZED ARTICLES

FIELD OF INVENTION

The present invention relates to chemical sterilization. More specifically, this invention relates to a method and system for removing the residue of sterilants, such as ethylene oxide (EO), from chemically-sterilized articles.

BACKGROUND OF THE INVENTION

Many surgical devices and materials must be sterilized prior to use for the health and safety of patients and hospital staff. Sterilization may be divided into high- and low-temperature sterilization. Generally, high-temperature sterilization is preferred since it is significantly faster than low-temperature sterilization. High-temperature sterilization involves exposing the articles to be sterilized to steam at temperatures ranging from about 250 to about 270° F. in an air-tight chamber. The process can be completed usually in less than about 2 hours. However, some articles, such as plastic articles and electrical components, cannot withstand such high temperatures and require low-temperature sterilization. Low-temperature sterilization is the focus of this invention.

Typically, low-temperature sterilization involves the use of chemical sterilants at temperatures from about 100 to about 200° F. Common chemical sterilants include, for example, EO, formaldehyde, hydrogen peroxide, chlorine dioxide, and ozone. In medical applications, EO is the most widely used sterilant. Standards for EO sterilization are set forth in *Good Hospital Practice: Ethylene Oxide Sterilization and Sterility Assurance* ANSI/AAMI ST41-1992.

Low-temperature sterilization is usually a two-step process performed in an air-tight chamber. In the first step (the sterilization step), the articles having been cleaned and wrapped in gas permeable bags are placed in the chamber. Air is then evacuated from the chamber by pulling a vacuum and perhaps by displacing the air with steam. In processes using EO as the sterilant, it is preferable to inject steam into the chamber to achieve a relative humidity that ranges preferably from about 30% to about 70%. Such humidities are found to maximize the sterilizing effectiveness of the EO sterilant which is introduced into the chamber after the desired relative humidity is achieved. After a period of time sufficient for the sterilant to permeate the wrapping and reach the interstices of the article, the sterilant and steam are evacuated from the chamber.

In the second step of the process (the aeration step), the articles are aerated to remove sterilant residues. Removing such residues is particularly important in the case of toxic sterilants, such as EO. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

Low-temperature sterilization is time-consuming. Although the sterilization step can be done in less than 3 hours, the aeration step typically requires from about 8 to about 10 hours. The time between when an article is sent for sterilization and when it is returned is called "turnaround time."

There is a need to reduce turnaround time. This need stems from cost cutting pressures applied to hospitals by government and insurance companies. Since articles being sterilized are not available for use, an inventory of articles must be kept on hand to accommodate the turnaround time. Such inventory can be expensive, often times costing the hospital millions of dollars. Consequently, a great deal of effort has been directed at reducing turnaround time, particularly the aeration step which represents the majority of the turnaround time.

Recent efforts have been successful at reducing turnaround time, but they tend to create other problems which are severe enough to restrict their implementation. For example, one prior art effort involves using sterilants other then EO, such as vapor phase hydrogen peroxide or peracetic acid, and smaller sterilization chambers. Although these sterilization chambers can turnaround articles more quickly, their small capacity limits their throughput. Additionally, the alternative chemical sterilants used in these sterilizers are not as versatile as EO.

Another prior art effort to reduce aeration time involves sorting devices by ease of aeration. For example, some materials tend to be less prone to sterilant residue and/or the sterilant residue can be removed more readily. Others materials can withstand higher temperatures. Every 8° F. increase in temperature can reduce sterilizing and aeration times by 50%. Therefore, by sorting articles according to their ability to withstand either higher temperatures or to retain low sterilant residue, they can be put on a "fast track" and avoid being grouped with other articles which require the use of lower temperatures or longer aeration times. Such an approach, however, is labor intensive and complicated since different operating conditions must be observed constantly. Additionally, the sorting approach runs the risk of articles being damaged or inadequately sterilized due to errors in grouping.

Yet another approach to the problem involves injecting supersaturated steam with the sterilant as described in U.S. Pat. No. 4,770,851. The supersaturated steam condenses on the articles and their wrapping. The condensed steam acts as a removal agent for the sterilant by condensing in the interstices of the article and then evaporating to carry the sterilant away. This approach, however, requires costly modification to existing systems. Additionally, the condensing of steam on articles and their wrapping can result in the formation of undesirable "wet packs." Wet packs compromise the sterilization process by providing a medium (water) in which bacteria live and migrate. Contact with water may also damage certain articles such as electronic components. Thus, this approach reduces time, but can increase the risk of inadequate sterilization of and damage to the articles.

Therefore, a need exists for a less time-consuming aeration procedure that can be practiced on all articles that require low-temperature sterilization without compromising sterilization or damaging the articles. The present invention fulfills this need among others.

DESCRIPTION OF THE INVENTION AND PREFERRED EMBODIMENTS

The present invention provides a system and method for aerating chemically-sterilized articles more efficiently by reducing the articles' adsorption of the sterilant. Adsorption is the ability of a substance ("adsorbent") to hold or otherwise concentrate a gas, liquid, or other dissolved substance ("adsorbate") on its surface. By introducing a competing adsorbate to the aeration process, the adsorbed sterilant on the surface of the article is at least partially displaced. Reducing the amount of adsorbed sterilant significantly improves aeration efficiency since adsorbed molecules are found to be particularly difficult to remove.

The difficulty in aerating chemically-sterilized articles appears to be related, at least partially, to the adsorption of the sterilant. This relationship is evident in the variable aeration rate of EO-sterilized articles. EO is considered specifically herein because it is the most common chemical sterilant and its residue tends to be relatively difficult to remove. It should be noted, however, that the underlying principles addressed herein also apply to other conventional sterilants, and that the discussion of EO herein should not be construed to limit the scope of the invention to just EO sterilization.

Figure 1:
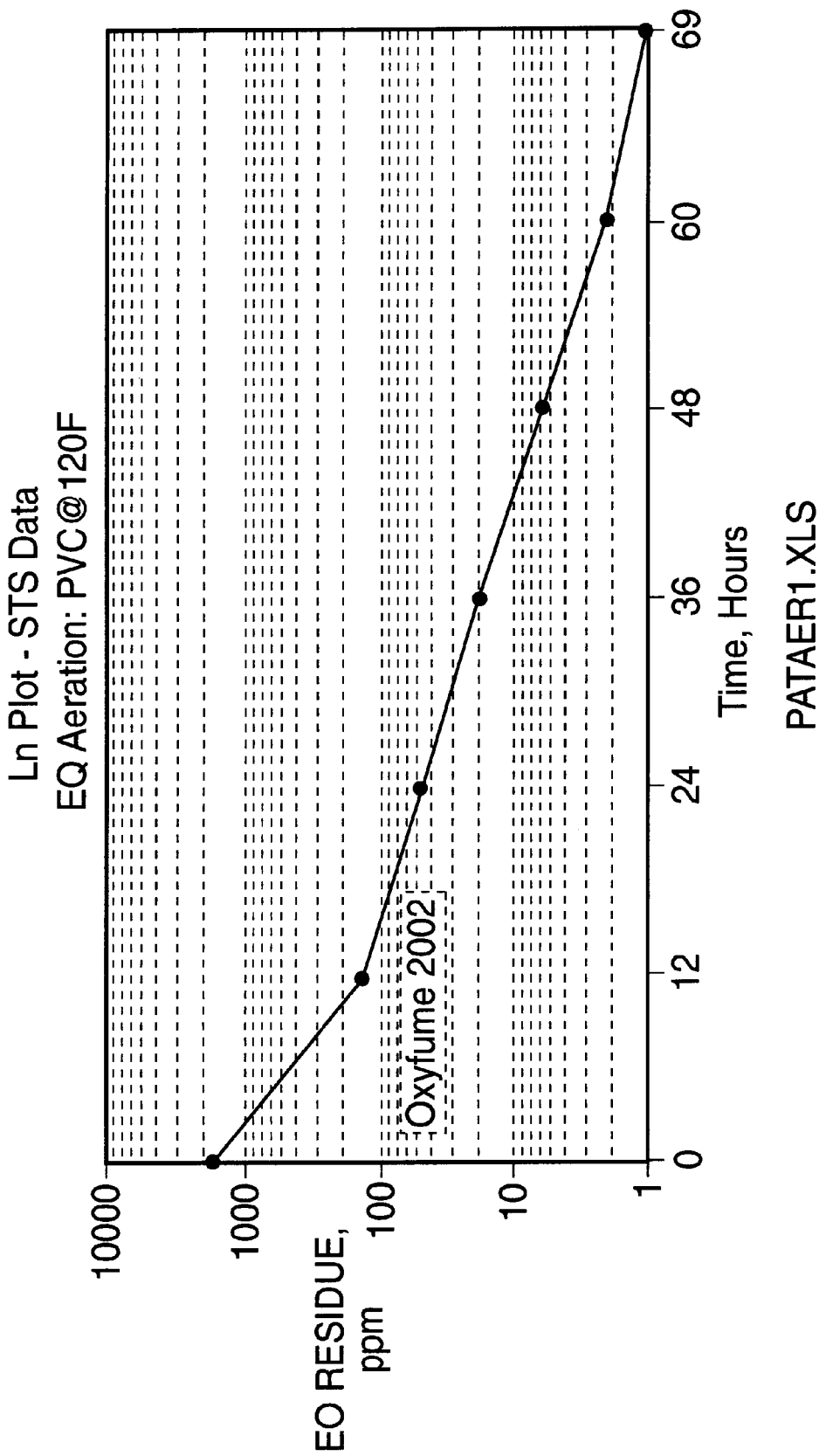
FIG. 1 shows a plot of the rate of EO residue removal from PVC plastic on a semi-logarithmic scale.

It has been observed that aeration of an EO-sterilized article is a two-phase process. In the first phase, EO removal is fast. For example, in the aeration of PVC exposed to 600 mg/l of EO sterilant (Oxyfume 2002®, AlliedSignal, Morristown, N.J.) for 135 minutes at 120° F., as shown in FIG. 1, EO decreased from 1828 ppm to 125 ppm in about 12 hours. This corresponds to a removal rate of −0.225 lnΔEOppm/hr. In the second phase, removal is considerably slower even on a logarithmic scale. To reduce EO concentration from 125 ppm to 1 ppm required 57 hours which corresponds to a removal rate of −0.085 lnΔEOppm/hr. This decrease in removal rate indicates that the EO residue removed in the second phase of aeration was more tightly held than the EO residue removed in the first phase.

The number of EO molecules above a surface containing adsorbed EO is measured by the partial pressure of EO (herein "$P_{EO}$"). As the hold of adsorbed EO increases, the EO molecules above the surface decrease, resulting in a decrease of $P_{EO}$. $P_{EO}$ is an equilibrium function of the amount of EO adsorbed per amount of surface (herein "$q_{EO}$"). In current aeration processes, these molecules are removed from the system by blowing EO-free air over the surface. The volume of air needed to remove the EO is inversely proportional to the rate of change of $P_{EO}$ with $q_{EO}$ ($\Delta P/\Delta q$). Because the surface attraction for EO increases almost exponentially with removal of successive layers of EO molecules, $\Delta P/\Delta q$ decreases exponentially and the volume of air needed to remove EO molecules will therefore increase exponentially.

The present invention not only identifies a probable cause for the difficulty in removing sterilant residue, but also provides an innovative solution aimed at the cause. The solution, as mentioned above, involves introducing one or more co-adsorbates during the aeration process to displace the sterilant. Since a sterilized article has limited surface area, the sterilant and co-adsorbate will compete for surface area and eventually reach equilibrium. The equilibrium is represented by the following general equation for multi-component adsorption:

$$q_{EO}/q_{lim} = k_{EO}f(P_{EO})/(1 + k_{EO}f(P_{EO}) + k_c f(P_c)) \tag{1}$$

wherein:

$q_{EO}$ is the quantity of EO adsorbed on a quantity of the material;

$q_{lim}$ is the maximum quantity of adsorbates on the quantity of material based on the adsorbent's "surface area," which, in the context of adsorption, relates to all exposed solid surfaces, typically of micron and angstrom dimensions, which, although not visible to the naked eye, are usually in the form of pores and crevices in, the material;

$k_{EO}$ an adsorbent constant for EO;

$k_c$ an adsorbent constant for the co-adsorbate;

$P_{EO}$ partial pressure of EO;

$P_c$ partial pressure of the co-adsorbate;

$f(P_{EO})$ corresponds to the quantify of EO on a specific absorbent surface as a function of the partial pressure of EO; and $f(P_c)$ corresponds to the quantify of co-adsorbate on the specific absorbent surface as a function of the partial pressure of the co-adsorbate.

Looking at Equation (1), it can be seen that if there is a co-adsorbate, C, during aeration, then the EO residue, $q_{EO}$, will be lower. For example, when PVC and Teflon were exposed to 4.5 psig of pure EO at 120° F. for 135 minutes, residual EO amounted to 3948 and 23 ppm, respectively. However, when the same materials were exposed to a blend of 4.5 psig of pure EO and 12 psig of a blend of HCFC-124 and HCFC-22 under the same conditions, residual EO amounted to 1828 and 14 ppm, respectively. Therefore, it can be seen that even though the partial pressure of EO remained the same, the HCFC co-adsorbate reduced the amount of residual EO by about half.

During the aeration step, as co-adsorbate enriched air is passed over the article, the partial pressure of EO drops while that of the co-adsorbate remains the same. This shifts the adsorption equilibrium, as expressed in Equation (1), such that adsorption of the co-adsorbate is favored. Over time, EO will be substantially displaced by the co-adsorbate. Therefore, rather than just removing adsorbed EO by lowering its partial pressure, the aeration of the present invention also removes adsorbed EO by displacing it with the co-adsorbate. This provides for more rapid aeration which can decrease turnaround time and residual EO levels.

Accordingly, one aspect of the invention is the provision of a method for aerating an article to remove sterilant residue. In a preferred embodiment, said method comprises exposing the article to at least one co-adsorbate under conditions such that said co-adsorbate remains above its dew point.

Another aspect of the invention is the provision of an apparatus for performing the above process. In a preferred embodiment, the apparatus comprises (a) a chamber; (b) air supply means for supplying said chamber with air; (c) co-adsorbate supply means for supplying said chamber with a co-adsorbate; (d) evacuating means for evacuating gases from said chamber; (e) regulation means for regulating the supply and evacuation of air and co-adsorbate into and out of said chamber; and (f) instructional means for instructing said regulation means to perform an aeration process of one or more articles, said aeration process comprising at least introducing co-adsorbate during aeration of said article.

Yet another aspect of the invention is the provision of a method of retrofitting existing sterilization apparatus to perform the method as described above. In a preferred embodiment, the method comprises reconfiguring the apparatus such that it injects steam not only during the sterilization phase, but also during the aeration phase.

Conventional aeration methods and apparatus can be adapted readily to the method and apparatus of the present invention. In a conventional aeration process, as described above, air washes and continuous aeration are used individually and in combination. Adapting these processes in accordance with the present invention simply requires exposing the co-adsorbate to the article by injecting the co-adsorbate into the chamber during the air wash or continuous aeration step.

Suitable co-adsorbates include any vaporized, non-toxic substance which has sufficient partial pressure at the operating temperature of the aeration step to displace at least a portion of the sterilant adsorbed by said article. Preferably, the co-adsorbate remains above its dew point at degassing temperatures. In a more preferred embodiment, the co-adsorbate has an adsorbed partial pressure of no less than about 1/10 that of EO for a similar adsorbed concentration at degassing temperatures. Examples of suitable co-adsorbates include, but are not limited to, steam, $CO_2$, hydrofluorocarbons (HFCs), such as pentafluoroethane (HFC-125), 1,1,1,2-tetrafluoroethane (HFC-134a), 1,1,1,3,3-pentafluoropropane (HFC-245fa), and 1,1,1,2,3,3,3-heptafluoropropane (HFC-227ea); hydrochlorofluorocarbons (HCFCs), such as chlorodifluoromethane (HCFC-22), and 2-chloro, 1,1,1,2 tetrafluoroethane (HCFC-124); chlorofluorocarbons (CFCs), such as trichlorofluoromethane (CFC-11) and dichlorodifluoromethane (CFC-12); halocarbons, such as brominated or iodinated hydrocarbons; and combinations of two or more thereof.

The particular selection of one or more co-adsorbates depends upon a variety of criteria, for example, the availability and cost of the co-adsorbate, the ease of implementing the co-adsorbate into existing and new systems, the effectiveness of the co-adsorbate in displacing EO, and other properties of the co-adsorbate such as toxicity, flammability, compatibility with other materials, and environmental acceptability. In most situations, selecting the co-adsorbate will usually involve optimizing these various criteria. For example, although one material may displace EO more readily at a given partial pressure than another material, its cost may be prohibitive. Accordingly, a less effective material may be more cost effective even though more of it is required. From the perspective of ease of implementation, the preferred co-adsorbate is probably steam since most existing sterilization apparatus already use steam in the sterilization step.

Preferably, the co-adsorbate is exposed to the article at or near its saturation point, but not beyond. High partial pressure of co-adsorbate is preferred since the degree of adsorption depends upon the partial pressure of the co-adsorbate (see Equation (1)). The partial pressure, however, should not be so high such that the co-adsorbate condenses at the operating temperature. Condensed co-adsorbate compromises the sterilization process and can damage certain articles being sterilized, for example, electrical devices.

In many cases, the operating conditions of the aeration process are limited by the materials being sterilized. As mentioned above, EO sterilization is employed generally for articles that can not withstand high temperatures. Therefore, the operating temperature of the EO sterilization should be no greater than about 250° F. Preferably, the operating temperature is no greater than about 200° F., and more preferably no greater than about 140° F.

In the case of a heated co-adsorbate such as steam, it should be injected into the chamber under conditions such that the temperature inside the chamber does not exceed a predetermined maximum operating temperature. This limitation can be observed in a variety of ways such as by slowly injecting the heated co-adsorbate into the aeration chamber, by intermittently injecting it, or by lowering its temperature. In the latter approach, the lower temperature requires a lower partial pressure to avoid condensation. Lowering the co-adsorbate's partial pressure, however, reduces its effectiveness as discussed below.

Maintaining a co-adsorbate at or below saturation for a certain temperature limits the partial pressure of the co-adsorbate. As is known, increasing the partial pressure of a vapor moves it closer to its dew point for a given temperature. Therefore, even though high partial pressures result in higher co-absorption (see Formula (1)), such pressure may also result in condensation.

Given these limitations, one of ordinary skill in the art can readily determine the preferred range of partial pressures and temperature of the co-adsorbate used. This determination is made simply by consulting the co-adsorbate's phase diagram. For example, steam at 200° F. and 140° F. has saturation partial pressures of about 11.5 psia and 2.9 psia, respectively. Therefore, in the preferred embodiment, the partial pressure of steam should be maintained at or below these levels when the chamber is maintained at the corresponding temperature.

Figure 2:
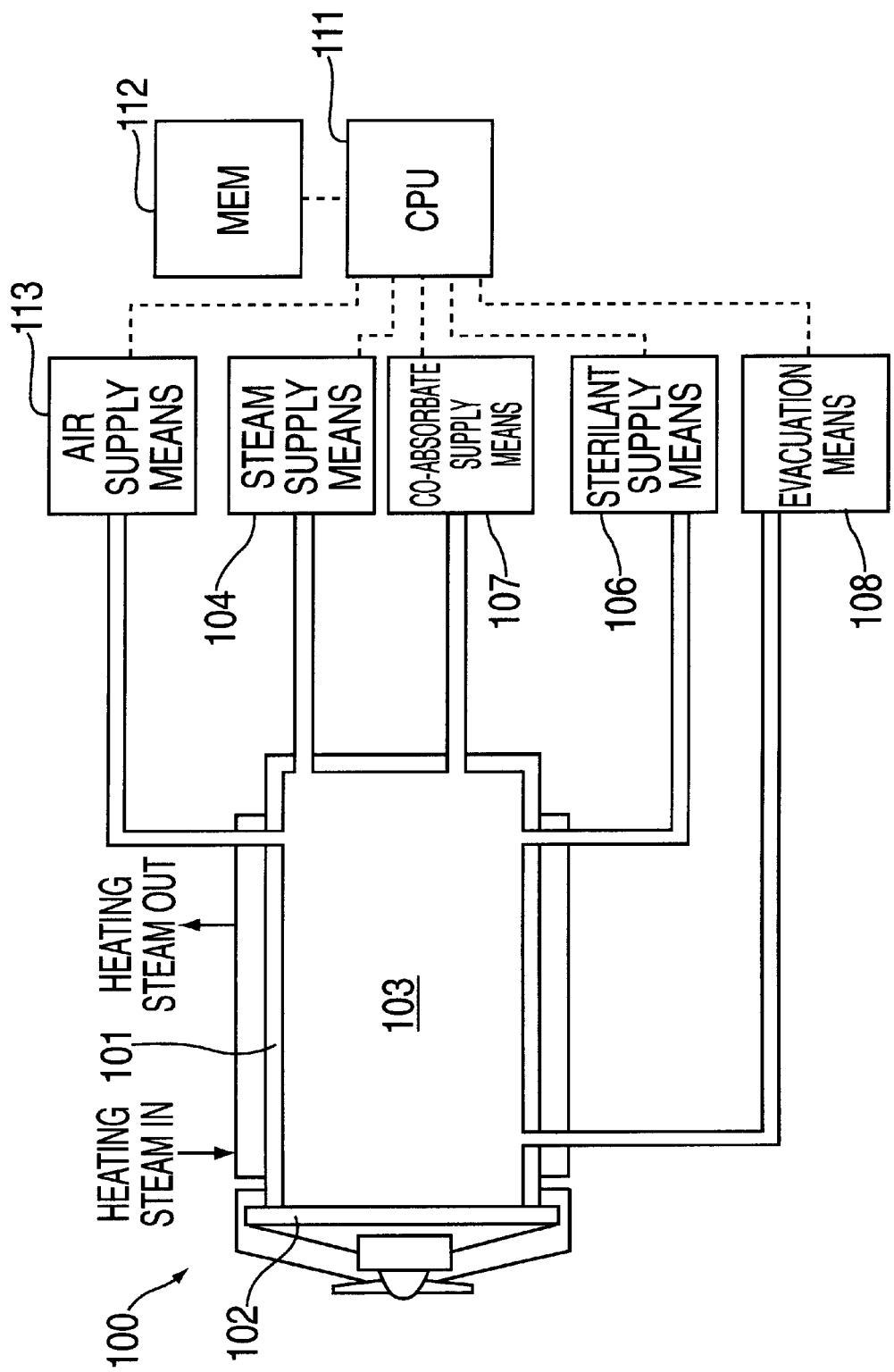
FIG. 2 shows a schematic diagram of an apparatus of the present invention.

The apparatus used to perform the process of the present invention is readily adaptable from conventional sterilization apparatus such as those manufactured by Steris Corporation (Mentor, Ohio) and Getinge Corporation (Rochester, N.Y.), and from dedicated aeration apparatus such as those used by medical device manufactures. Referring to FIG. 2, a sterilization apparatus 100 of the present invention is shown. Like any conventional system, the apparatus 100 comprises a containment 101 having a door 102 that provides access to a chamber 103 in which the articles to be sterilized are placed.

For the sterilization step, there are EO and steam supply means 106, 107, respectively, for supplying EO and steam to the chamber 103. Such means are known in the art and may involve systems of fans/pumps, heat exchangers, valving, filters, and connective conduit. Evacuation means 108 are used to evacuate the EO and steam from the chamber. Again, such means are known in the art and include, for example, vacuum pumps, valving, filters, and connective conduit (see also U.S. Pat. No. 4,770,851 for a description of a suitable sterilizer).

The aeration step of the sterilization process is performed usually by hospitals in the same chamber as the sterilization step, and by medical device manufacturers in a different enclosure. Nevertheless, the basic apparatus for aeration remains the same. Air supply means 113 supply the chamber 103 with air. Such means may comprise any conventional filtered air delivery system. To maintain the chamber 103 at preferred operating temperatures, the apparatus can include heating means, such as, for example, internal coils, heating strips, and steam jackets. In FIG. 2, the apparatus 100 is depicted having a steam jacket 110.

Since the entire sterilization process can take a long time, typically about 800 to about 900 minutes, and since the chamber should be maintained at specific temperatures and pressures during this period, the apparatus is usually automated. The injection of EO, steam and air into the chamber and their subsequent evacuation is controlled by regulation means which typically comprises a central processing unit (CPU) 111. The CPU 111 may be a discrete processor, or a combination of processors, configured in a personal computer, controller, work station, main frame or the like. Such CPUs are known in the art. The CPU 111 receives instructions from instructional means to control the various means to perform the sterilization process as described above. Typically, the instructional means is memory 112 loaded with a program of instructions. Memory 112 can be any computer readable medium, such as RAM, ROM or PROM, capable of containing such instructions.

The sterilization apparatus described above is basically conventional. The apparatus of the present invention provides for the injection of a co-adsorbate during the aeration step. In the preferred embodiment, the co-adsorbate is steam, which is already used in the sterilization step. Accordingly, using steam as the co-adsorbate avoids the need to incorporate another co-adsorbate supply means 107 in the apparatus. With automated apparatus, the only change consists of a modification to the instructional means resident such that the CPU 111 injects steam not only during the sterilization step, but also during the aeration step. Such a modification would be obvious to someone skilled in the art in light of this disclosure. For example, it may involve up-loading a new program into memory 112. The program may be adapted to function on known and anticipated operating platforms, and may be stored on any computer readable medium such as, for example, a disk, tape, CD ROM, RAM or PROM. Alternatively, modifying the CPU's instructional means may involve replacing a ROM or PROM chip with one containing the appropriate set of instructions.

In other embodiments of the present invention involving, for example, either the use of an additional or alternative co-adsorbate, or the use of dedicated aeration apparatus having no steam supply means, the incorporation of co-adsorbate supply means 107 is required. Such supply means, however, are known in the art, and include, for example, pressurized tanks with regulator valving.

EXAMPLES

The comparative and illustrative examples below show the effectiveness of the aeration techniques provided by the present invention. In these examples, a conventional 30 ft$^3$ sterilizer was used to sterilize and aerate PVC tubes. PVC is known to be difficult to aerate and has been used frequently as a component material in medical devices. After aeration, EO residue was measured. Aeration is considered satisfactory, under current standards (1978 FDA recommendation), if EO residue is below 25 ppm. Data from the sterilization and aeration steps is presented in Table 1.

TABLE 1

Example Summary

| STEP | Comparative Example | Illustrative Example |
|---|---|---|
| STERILIZATION | | |
| Preheat | | |
| Time (min.) | 1.1 | 1.1 |
| Temp (° F.) | 121 | 121 |
| Pre-Vac | | |
| Time (min.) | 14.2 | 15.0 |
| Humidify | | |
| Time (min.) | 39.4 | 33.3 |
| RH (%) | 45 | 45 |
| Gas Charge | | |
| Time (min.) | 8 | 8 |
| Conc. (mg EO/liter) | 435 | 435 |
| Amount (lb gas/cycle) | 8.1 | 8.1 |
| Sterilize | | |
| Time (min.) | 180 | 180 |
| Temperature (° F.) | 133 | 133 |
| Pressure (psig) | 21 | 21 |
| Exhaust | | |
| Time (min.) | 1.5 | 1.5 |
| AERATION | | |
| Air Wash | | |
| Time (min.) | 484 | 349 |
| Temp (° F.) | 132 | 135 |
| # Cycles | 31 | 23 |
| Evacuate (min.) | 12.6 | 12.8 |
| Pressurize (min.) | 3.0 | 2.4 |
| Time per Cycle (min.) | 15.6 | 15.2 |
| Total airwash, min | 484 | 349 |
| Steam pulse rate (min. on/off) | N/A | 1/5 |
| Steam line pressure (psig) | N/A | 18 |
| Estimated steam line temp. (° F.) | N/A | 260 |
| Estimated change in chamber pressure during injection (psi) | N/A | 0.3 |
| Estimated % RH @ air wash start | N/A | 45% |
| Estimated peak % RH during air wash | N/A | 90% |
| No. of Air wash cycles without steam | 31 | 2 |
| Total Cycle Time | 730 | 590 |
| Average EO residue | 95 | 12 |

COMPARATIVE EXAMPLE

This example illustrates a known sterilization procedure performed under optimized conditions. The aeration step of this sterilization procedure constituted air washes. The air washes comprised a series of fifteen minute cycles of pulling a vacuum and repressurizing with air. The temperature was maintained at about 132° F.

After a total air wash time of 484 minutes, EO residue on PVC tubes is reduced to 95 ppm.

ILLUSTRATIVE EXAMPLE

In this example, steam was injected during air washes as detailed in Table 1 and 2. Steam was introduced intermittently so that the chamber was not heated to a temperature that would damage the medical devices. During each air wash, a cycle was repeated in which steam was injected for up to 0.5 minutes increasing the chamber pressure by about 0.3 psia, then turned off for 2.5 minutes. These cycles were performed 21 of the 23 air washes conducted. No steam was injected during the last two air washes to allow for the removal of moisture remaining in materials and chamber void spaces. Air wash temperature was increased from 132° F. to 135° F.

After a total air wash time of only 349 minutes, EO residue on PVC tubes is reduced to 12 ppm. Well within the 1978 FDA guidelines, with a total cycle time of less than 10 hours—allowing two cycles per day to be run on the sterilizer. This air wash cycle is not only 2 hours shorter than the comparative example, but also the EO residue is 85% lower.

What is claimed is:

1. A method for aerating an ethylene oxide-sterilized article to remove residual ethylene oxide, said method comprising:
    exposing said article to at least one co-adsorbate under conditions such that said co-adsorbate remains above its dew point, said co-adsorbate having a partial pressure under said conditions sufficient to displace at least a portion of the ethylene oxide adsorbed by said article.

2. The method of claim 1, wherein said co-adsorbate is selected from the group consisting of steam, $CO_2$, HFCs, HCFCs, CFCs, and halo-carbons.

3. The method of claim 2, wherein said co-adsorbate is steam.

4. The method of claim 3, wherein said operating conditions comprise a temperature no greater than about 200° F. and a partial pressure of steam no greater than about 11.5 psia.

5. The method of claim 4, wherein said temperature is no greater than about 140° F. and said partial pressure of steam is no greater than about 2.9 psia.

6. The method of claim 5, wherein said partial pressure of steam is at about saturation.

7. The method of claim 1, wherein said operating conditions comprise a temperature no greater than about 140° F.

8. The method of claim 7, wherein said co-adsorbate has a partial pressure at about saturation.

9. The method of claim 1, wherein exposing said article to said co-adsorbate comprises performing one or more air washes until ethylene oxide residue is reduced to a predetermined level, said air washes comprising:
    injecting air and said co-adsorbate into a chamber containing said article; and
    evacuating said air and said co-adsorbate after a predetermined period.

10. The method of claim 9, wherein a plurality of air washes are performed and at least the last air wash performed contains no co-adsorbate.

11. The method of claim 10, wherein said co-adsorbate is steam.

12. The method of claim 1, wherein exposing said article to said co-adsorbate comprises performing a continuous aeration until ethylene oxide residue is reduced to an acceptable level, said continuous aeration comprising:
    continuously injecting air and said co-adsorbate into a chamber containing said article; and
    continuously evacuating air and co-adsorbate from said chamber at about the same rate as said air and said co-adsorbate are injected into said chamber.

13. The method of claim 12, wherein said co-adsorbate is steam.

14. A method for aerating a chemically-sterilized article to remove residual sterilant, said method comprising:
    exposing said article to at least one co-adsorbate under conditions such that said co-adsorbate remains above its dew point and has a partial pressure under said conditions sufficient to displace at least a portion of the sterilant adsorbed by said article,
    wherein exposing said article to said co-adsorbate comprises performing a continuous aeration until sterilant residue is reduced to an acceptable level, said continuous aeration comprising:
    continuously injecting air and said co-adsorbate into a chamber containing said article; and
    continuously evacuating air and co-adsorbate from said chamber at about the same rate as said air and said co-adsorbate are injected into said chamber.

15. The method of claim 14, wherein said co-adsorbate is steam.

* * * * *